United States Patent [19]

Redikultsev et al.

[11] Patent Number: 4,621,060

[45] Date of Patent: Nov. 4, 1986

[54] APPARATUS FOR TAKING SAMPLES FROM A FERMENTER

[75] Inventors: Jury V. Redikultsev; Mikhail G. Maximov, both of Puschino Moskovskaya, U.S.S.R.

[73] Assignee: Institut Biokhimii I Fiziologii Mikroorganizmov Akademii Nauk SSSR, Puschino, U.S.S.R.

[21] Appl. No.: 598,340

[22] PCT Filed: Jul. 30, 1982

[86] PCT No.: PCT/SU82/00026

§ 371 Date: Mar. 23, 1984

§ 102(e) Date: Mar. 23, 1984

[87] PCT Pub. No.: WO84/00559

PCT Pub. Date: Feb. 16, 1984

[51] Int. Cl.$^4$ ............... C12M 1/26; C12M 1/00; C12Q 1/24; G01N 1/00
[52] U.S. Cl. ................................. 435/292; 435/30; 435/287; 422/103; 422/119; 141/89; 141/104
[58] Field of Search ............... 435/287, 292, 293, 294, 435/296, 30; 422/103, 119; 73/863.01, 863.71, 864.34, 864.35; 141/101, 104, 89, 146, 285

[56] References Cited

U.S. PATENT DOCUMENTS 2,566,306  9/1951  Beesch ........................... 435/292
4,047,547  9/1977  Rechsteiner et al. ........... 73/863.86
4,113,437  9/1978  Duff et al. ....................... 422/64 X
4,209,585  6/1980  Lloyd et al. .................. 435/292 X
4,210,724  7/1980  Sogi et al. ......................... 435/292

FOREIGN PATENT DOCUMENTS 2752284  6/1978  Fed. Rep. of Germany ... 73/863.86

Primary Examiner—David M. Naff
Assistant Examiner—Randall E. Deck
Attorney, Agent, or Firm—Burgess, Ryan & Wayne

[57] ABSTRACT

The present invention is directed to an apparatus for taking samples from a fermenter having such a construction as to enable sterilization of the equipment for taking the sample simultaneously with the procedure of sample taking. The possibility of inadvertently contaminating a fluid being sampled is prevented. The apparatus comprises a sampler (1) provided at the inlet with a valve (3), a by-pass valve (27) mountable at the outlet of a fermenter (39), and a separating chamber (19) between the valves (3) and (27). The chamber (19) has a nipple (40) with a valve (28) for feeding a sterilizing agent to the sampler (1). An additional valve (7) is secured at the inlet of the sampler (1), a housing of the valve (3) functioning as a shut-off member of this valve (7). The chamber (19) is capable of reciprocating motion in the direction of travel of the shut-off members (4) and (6) and engagement therewith.

2 Claims, 2 Drawing Figures

APPARATUS FOR TAKING SAMPLES FROM A FERMENTER

FIELD OF THE INVENTION

This invention relates generally to microbiology, and more particularly concerns an apparatus for taking samples from a fermenter.

BACKGROUND OF THE INVENTION

There is known a device for taking samples from a fermenter comprising a sampler and a by-pass valve, this device being widely known in laboratory research practice.

The use of such a device for sample taking necessitates the employment of an open flame to treat conduits wherethrough a liquid being tested is passed from the fermenter to the sampler, the nipple of the sampler being necessarily immersed into an antiseptic solution. The sampler normally has a cotton plug which is removed in the flame zone during sample taking and set into place after terminating the sample taking procedure. The by-pass valve is provided with a clamp handled by one more attendant. The device described heretofore is difficult to operate, while the range of its possible application is rather limited, since it is impossible to take samples of explosive or inflammable fluids.

There is also known a device for taking samples from a fermenter comprising a by-pass valve mountable at the outlet of the fermenter, and a sampler having its own by-pass valve arranged at the inlet thereof.

The by-pass valve of the sampler has a spring-loaded rod, an annular groove and a sealing element, whereas the by-pass valve of the fermenter is provided with a spring-loaded rod and an annular projection defining during cooperation with the annular groove of the sampler valve a hermetically sealed separating chamber for the passage of a sample fluid therethrough (cf., e.g., USSR Inventor's Certificate No. 726,833, published 1979).

Prior to taking a sample from the fermenter, it is necessary that the sampler be sterilized and an underpressure or vacuum be induced therein, whereupon the sampler must be hermetically coupled with the by-pass valve of the fermenter, and by depressing the sampler the latter is filled with a culture suspension to be examined.

However, inherent in the device of the above construction is a disadvantage in that it fails to maintain sterility of the mating surfaces of the by-pass valves of the sampler and fermenter, whereby the fluid to be tested is susceptible to contamination after this fluid passes the separating chamber, the fluid may also be contaminated both in the fermenter and in the sampler.

SUMMARY OF THE INVENTION

The present invention is directed toward the provision of an apparatus for taking samples from a fermenter having such a construction as to enable sterilization of the equipment for sample taking simultaneously with the procedure of sample taking and prevention of the possibility of inadvertently contaminating a fluid being sampled, as well as to make the sample taking procedure more amenable to automation.

The aim of the invention is attained by that in an apparatus for taking samples from a fermenter comprising a by-pass valve mountable at the outlet from the fermenter, a sampler having its own valve at the inlet thereof, and a separating chamber between the valves, according to the invention, the separating chamber is provided with a nipple having a valve for feeding thereinto a sterilizing agent, whereas at the inlet to the sampler there is disposed an additional valve with a housing of the valve arranged at the inlet of the sampler functioning as a shut-off member of this additional valve, the separating chamber being capable of reciprocating motion in the direction of travel of the shut-off members of the main and additional valves of the sampler, and of cooperation with these members and with the housing of the additionaal valve of the sampler so that in one of the extreme positions of the chamber a hermetically sealed passage would be formed for evacuation of a sterilizing agent from the sampler.

In order to make the sample taking procedure more efficient, it is preferable that the apparatus be provided with a turret having a drive means, and a heat exchanger and a drum with sockets for securing the samplers, both the heat exchanger and the drum being secured on a shaft of the turret; the separating chamber being preferably disposed under the drum such that its outlet sleeve would assume a position opposite to the shut-off member of the main valve of the sampler when the latter is secured in the socket.

The apparatus for taking samples from a fermenter constructed according to the features of the present invention makes it possible to combine sterilization of sample taking elements in one cycle with the sample taking procedure, hermetic sealing and cooling. It also enables one to take samples of various gas mixtures without disturbing their compositions. The apparatus further assures taking samples of liquids from anaerobic processes and prevents the penetration of air to the sample tube for preservation of the sample taken.

BRIEF DESCRIPTION OF THE DRAWINGS

The invention will now be described in greater detail with reference to a specific embodiment thereof taken in conjunction with the accompanying drawings, in which.

BEST MODE OF CARRYING OUT THE INVENTION

Figure 1:
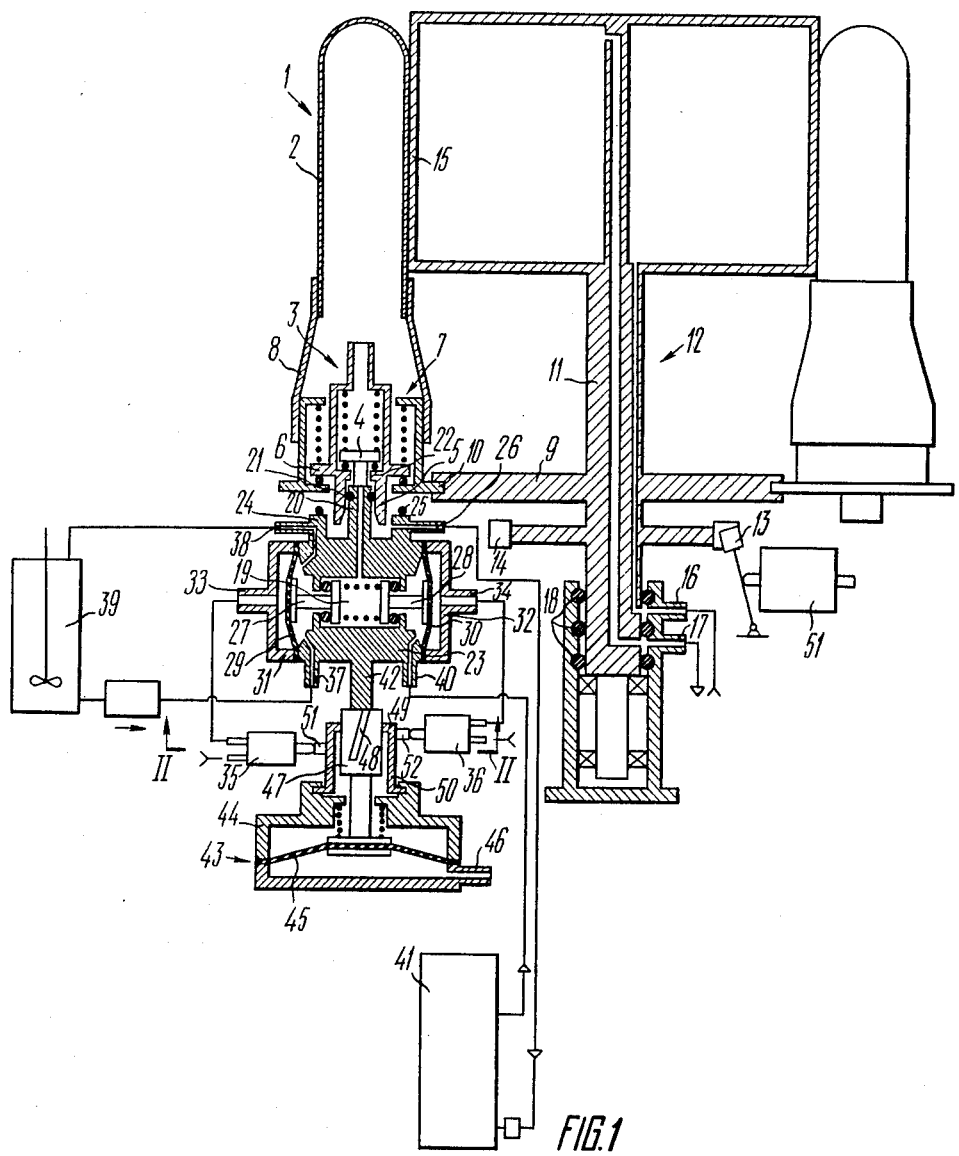
FIG. 1 is a longitudinal sectional view of an apparatus for taking samples from a fermenter according to the invention.

An apparatus for taking samples from a fermenter embodying the features of the present invention comprises a sampler 1 (FIG. 1) which includes a tube 2 to receive a fluid to be examined, a valve 3 disposed at the inlet to the test tube 2 and having a shut-off member 4 and a sleeve 5 for introducing into the test tube 2 a sterilizing agent (steam) or the fluid being examined, the housing of this valve 3 also functioning as a shut-off member 6 of an additional valve 7 serving to discharge a steam condensate and hermetically coupled with the test tube 2 by means of an elastic sealing collar 8. The sampler 1 is disposed in a socket of a rotating drum 9 and fixed in position therein by means of a flange 10 of the additional valve 7.

The rotating drum 9 is secured on a shaft 11 of a turret 12 rotatable by a propelling device 13 and a gear 14 rigidly affixed on the shaft 11. In addition, a heat exchanger 15 is secured on the shaft 11 of the turret 12 to cool the samplers 1, this heat exchanger 15 having nipples 16 and 17 for receiving and discharging a cooling agent, respectively, the nipples being separated on the shaft 11 by sealing O-rings 18. Further, the apparatus comprises a separating chamber 19 provided with an outlet sleeve 20 having a sealing O-ring 21 to assure a hermetic connection to the sleeve 5 of the valve 3. The separating chamber 19 is arranged such that its sleeve 20 is opposite the shut-off member 4 of the valve 3, and during reciprocating motions of the chamber 19 it is capable of cooperating with the shut-off member 4 and with an inner shoulder 22 provided in the sleeve 5, that is with the shut-off member 6 of the additional valve 7.

In a plane substantially perpendicular to the sleeve 20, the housing 23 of the separating chamber 19 has a flange element 24 with a sealing O-ring 25 to assure a hermetic coupling with the flange 10 of the additional valve 7, this housing 23 being also provided with a nipple 26. When the valve 7 is open, it forms with the nipple 26 a hermetic passage for discharging from the sampler 1 of the sterilizing steam condensate. The chamber 19 has two coaxial valves 27 and 28. In order to control the valves 27 and 28, in a plane substantially perpendicular to the axis of travel of the shut-off members of these valves the housing 23 has hermetically connected thereto by means of membranes 29 and 30 flanges 31 and 32 with nipples 33 and 34, respectively, for feeding compressed air from pneumatic actuators 35 and 36 to open the valves 27 and 28. The inlet of the bypass valve 27 is provided with nipples 37 and 38 to recycle the liquid being examined from the fermenter indicated at 39. At the inlet to the valve 28 there is disposed a nipple 40 for delivering steam from a steam source 41. For effecting reciprocating motions of the chamber 19 its housing 23 is rigidly connected to a push rod 42 of a pneumatically operated drive means 43.

Figure 2:
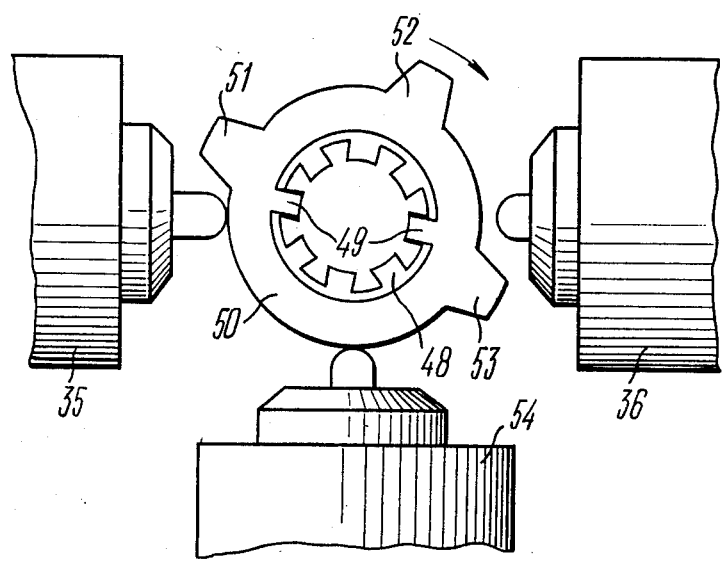
FIG. 2 is a section taken along the line II—II in FIG. 1, an enlarged view.

The pneumatically operated drive means 43 ensures automatic control of the apparatus and is comprised of a housing 44 hermetically separated by a flexible membrane 45 into two chambers, one of these chambers having a nipple 46 for introducing pneumatic control pulses, whereas the other chamber has the push rod 42 secured to a membrane 45. An extension piece 47 is arranged on the push rod 42 having grooves 48 (see also FIG. 2) arranged at an angle relative to the centerline thereof, these grooves receiving two inner projections 49 of a sleeve 50 for turning at a predetermined angle during reciprocations of the push rod 42. The sleeve 50 has on the outer side thereof three lugs 51, 52 and 53 for opening the corresponding pneumatic actuators 35 and 36 for controlling the feed of the fluid being examined and steam, and for opening a pneumatic actuator 54 for turning the drum 9 when replacing the sampler 1 (FIG. 1).

The apparatus according to the invention operates as follows.

In the initial position the samplers 1 are secured in sockets of the rotating drum 9 about the periphery of the heat exchanger 15 and are affixed therein by means of the flanges 10.

The membrane 45 of the pneumatically operated drive 43 is in its lowest position, the pneumatic actuators 35, 36 and 54 being disengaged, the compressed air not being fed to the membranes 29 and 30, the valves 3, 7, 27 and 28 being closed, and the sleeve 20 of the separating chamber 19 being disconnected from the sleeve 5 of the valve 3. The fluid being examined recycles through the nipples 37 and 38, whereas the sterilizing agent (steam) is admitted to the nipple 40 from the source 41.

When a controlling pneumatic pulse enters through the nipple 46 to the interior of the pneumatically operated drive 43 underlying the membrane 45, the latter is caused to move and through the pushrod 42 to act on the housing 23 of the separating chamber 19 for this chamber to be displaced to the upmost position. Therewith, at first, the sleeve 20 is received by the nipple 5 coupling hermetically therewith through the sealing O-ring 21 and thereafter acting on the shut-off member 4 of the valve 3 (as seen best in FIG. 1) and causing this valve 3 to open; during a further travel the sleeve 20 comes into engagement with the inner shoulder 22 of the shut-off member 6 of the additional valve 7 the opening of which is accompanied by a hermetic coupling of the flange 10 with the flange 24 through the sealing O-ring 25 and formation of a hermetic passage for evacuation of the steam condensate from the sampler 1. Concurrently, during the travel of the push rod 42 the projections 49 of the sleeve 50 slide in the grooves 48 to turn the sleeve 50 an angle at which the lug 52 engages with the pneumatic actuator 36 to cause it to open for compressed air acting on the membrane 30 to open the valve 28 wherethrough steam enters the sampler 1 and is discharged therefrom in the form of a steam condensate along the hermetic passage through the open valve 7 and the nipple 26.

Upon termination of the cycle for sterilizing the sampler 1, a subsequent pneumatic pulse is delivered to the pneumatically operated drive 43 to cause a partial lowering of the push rod 42. Therewith, the shut-off member 6 of the additional valve 7 descends thereby closing the valve 7, the pneumatic actuator 36 is brought out of engagement with the lug 52 of the sleeve 50, the compressed air fails to act on the membrane 30, and the valve 28 is caused to close, thus stopping the supply of steam to the sampler 1. Simultaneously with the downward travel of the push rod 42 the projections 49 of the sleeve 50 tend to slide in the grooves to turn the sleeve 50 a subsequent angle at which the lug 51 engages with the pneumatic actuator 35 to open it for the compressed air to act in turn on the membrane 29 and open the valve 27 wherethrough a fluid to be tested is fed to the cooled sampler 1 wherein a vacuum is induced due to condensation of steam. Subsequent to the sample taking cycle a successive controlling pneumatic pulse is fed to the pneumatically operated drive 43, which pulse acts to lower the push rod 42 to its initial position; therewith, the sleeve 20 is brought out of engagement with the shut-off member 4 and inlet sleeve 5 for the valve 3 to close.

The movement of the push rod 42 is accompanied by turning of the sleeve 50, whereby the lug 51 fails to engage with the pneumatic actuator 35 for the latter to be disengaged and close the valve 27. The projections 49 of the sleeve 50 are again caused to slide in the grooves 48 to turn the sleeve 50 yet another angle at which the lug 53 is brought in engagement with the pneumatic actuator 54 which delivers a signal to the propelling device 13 whereby the gear 14 turns the drum 9 to change the sampler 1 and return all the elements of the apparatus into their initial position.

INDUSTRIAL APPLICABILITY

The proposed apparatus for taking samples from a fermenter can find application in microbiological and pharmaceutical production facilities, for example, for sterilized filling of ampoules with medicinal preparations, as well as in food and chemical industries.

We claim:

1. An apparatus for taking samples from a fermenter having an outlet, comprising:
- a first by-pass valve provided at the outlet of a fermenter;
- a sampler having an inlet and an axis;
- a second valve provided at the inlet of said sampler and having a housing;
- a shut-off member of said second valve provided in said housing to move along the axis of said sampler;
- a separating chamber provided between said first and second valves;
- an outlet sleeve of said separating chamber located along said axis of said sampler;
- a nipple provided in said chamber to feed a sterilizing agent thereinto;
- a third valve provided between said nipple and said chamber;
- a fourth valve provided at said inlet of said sampler;
- a housing of said fourth valve provided coaxially to said housing of the second valve;
- said housing of the second valve having an annular projection functioning as a shut-off member of said fourth valve;
- said separating chamber being reciprocable in a direction of movement of said shut-off member of the second valve to first and second extreme positions and an intermediate position;
- all of said valves being closed in said first extreme position;
- the outlet sleeve of said chamber simultaneously engaging said housing of the second and fourth valves in said second extreme position to form a hermetic passage in which the sterilizing agent is supplied to said sampler through said second valve and evacuated through said fourth valve; and
- the outlet sleeve of the chamber engaging only said shut-off member of the second valve in said intermediate position to form a hermetic passage for providing communication between said fermenter and said sampler.

2. An apparatus as claimed in claim 1, further comprising:
- a turret including a drum having sockets having a plurality of samplers mounted therein;
- drive means for rotating said turret about an axis thereof;
- a heat exchanger extending along the axis of rotation of said turret;
- said separating chamber being located under a socket of said drum so that said outlet sleeve of said separating chamber is located opposite the shut-off member of said second valve of the sampler mounted in said socket.

* * * * *